United States Patent [19]

Kerr et al.

[11] 4,222,836
[45] Sep. 16, 1980

[54] ACIDIC AGAR GEL ELECTROCHROMATOGRAPHY OF GLYCOHEMOGLOBINS

[75] Inventors: Robert J. Kerr, Painted Post; Milos Stastny, Corning, both of N.Y.

[73] Assignee: Corning Glass Works, Corning, N.Y.

[21] Appl. No.: 44,472

[22] Filed: Jun. 1, 1979

[51] Int. Cl.$^2$ .................. G01N 33/16; G01N 27/26
[52] U.S. Cl. ..................... 204/180 G; 23/230 B; 424/12
[58] Field of Search .................. 204/180 G, 299; 23/230 B; 424/12

[56] References Cited

U.S. PATENT DOCUMENTS

| | | | |
|---|---|---|---|
| Re. 24,752 | 12/1959 | Ressler | 204/180 G |
| 3,497,437 | 2/1970 | Louderback et al. | 204/180 G |
| 3,558,459 | 1/1971 | Granstrand et al. | 204/180 G |
| 3,607,695 | 9/1971 | Schneider | 204/180 G X |
| 3,692,654 | 9/1972 | Svendsen | 204/180 G X |

*Primary Examiner*—Arthur C. Prescott
*Attorney, Agent, or Firm*—William E. Maycock; Clinton S. Janes, Jr.

[57] ABSTRACT

Glycosylated hemoglobins are separated from other hemoglobin variants by electrochromatography on an agar gel at an acidic pH which utilizes:

A. an agar gel having a wet thickness of from about 0.1 to about 0.5 mm.,

B. a citrate gel buffer having a citrate concentration of from about 0.02 to about 0.05 M and a pH of from about 5.8 to about 6.8, C. a citrate well buffer having a citrate concentration of from about 0.05 to about 0.1 M and a pH from about 6.0 to about 6.5, and D. a potential of from about 25 to about 100 volts.

18 Claims, No Drawings

ACIDIC AGAR GEL ELECTROCHROMATOGRAPHY OF GLYCOHEMOGLOBINS

BACKGROUND OF THE DISCLOSURE

One of the main difficulties in establishing whether or not there is a relationship between the degree of hyperglycemia and the long-term complications of diabetes is the lack of a reliable, objective method for assessing diabetic control. It recently has been suggested, however, that the measurement of glycosylated derivatives of normal hemoglobin, such as hemoglobin $A_{1c}$, can be an indicator of such diabetic control. See, for example, D. Gonen and A. H. Rubenstein, *Diabetologia*, 15, 1 (1978). Such derivative of hemoglobin is formed by the post-transcriptional glycosylation of hemoglobin $A_0$ (adult hemoglobin) at the terminal valine moiety of the beta chain. Such glycosylation is a slow chemical reaction which occurs throughout the life-span of the erythrocyte (about 120 days), the prevailing plasma glucose concentration being the most important factor governing the quantity of hemoglobin $A_{1c}$ formed.

Although a more rapid electrophoretic mobility of glycosylated hemoglobin was demonstrated by agar gel electrophoresis as early as 1957, quantitative data were not obtained by this method. The proportions of such hemoglobin only appeared to be much greater in some diabetic subjects than in others. Even those who first noticed glycosylated hemoglobin on the agar gel were not able to separate the glycosylated fraction to the extent that it could be quantified. S. Rahbar et al., *Biochem. and Biophys. Res. Comm.*, 36, 838 (1969). Consequently, most of the quantitation studies have been performed by chromatography. D. W. Allen et al., *J. Am. Chem. Soc.*, 80, 1628 (1958).

It since has been demonstrated by many investigators that there was indeed a quantitative importance of glycosylated hemoglobin determinations for the assessment of the status of sugar control in diabetic patients. However, an elaborate chromatographic separation was almost universally adopted. See, e.g., W. R. Holmquist and W. A. Schroeder, *Biochem. Biophys. Acta*, 82, 639 (1964) and L. A. Trivelli et al., *N. Engl. J. Med.*, 281, 353 (1971). By such procedures, it was demonstrated that diabetic patients typically show a 2-fold increase in the level of hemoglobin $A_{1c}$, the main component of glycosylated hemoglobins found in the peripheral blood.

The clinical importance of the glycosylated hemoglobin parameter in diabetic control and the relatively small span between normal and abnormal values calls for a rapid, routine assay of glycosylated hemoglobins which can be quantified with sufficient precision to reveal disturbances in sugar metabolism. Several modifications of minicolumn chromatographic procedures have been published and even introduced commercially for the quantitative assessment of glycosylated hemoglobins. Almost as many criticisms of these procedures appeared, citing the lack of precision. More laborious techniques such as isoelectric focusing and immuno techniques based on pure glycosylated hemoglobin antigenicity were suggested, but have not become accepted for routine clinical assays because of the sophisication of isoelectric focusing methodology and the difficulties in obtaining pure, specific antibody.

SUMMARY OF THE INVENTION

Accordingly, the present invention provides, in a method for discretely separating glycohemoglobins from nonglycosylated hemoglobins by citrate agar gel electrochromatography in which the gel buffer has a citrate concentration of 0.05 M and a pH of 6.2, the improvement which comprises employing:
  A. an agar gel having a wet thickness of from about 0.1 to about 0.5 mm.,
  B. a citrate gel buffer having a citrate concentration of from about 0.02 to about 0.05 M and a pH of from about 5.8 to about 6.8,
  C. a citrate well buffer having a citrate concentration of from about 0.05 to about 0.1 M and a pH of from about 6.0 to about 6.5, and
  D. a field strength of from about 5 to about 20 volts per cm.

The present invention is useful for discretely separating glycohemoglobins from hemoglobin and other hemoglobin derivatives. Furthermore, the method of the present invention is capable of separating hemoglobin $A_{1c}$, from the remaining $A_1$ hemoglobin derivatives.

DETAILED DESCRIPTION OF THE INVENTION

The theoretical basis of the separation described and claimed herein can be characterized as electrochromatography, which term perhaps is more appropriate than the term "electrophoresis" because of (1) the migration and separation of the hemoglobins being achieved largely by the combination of interactions between oppositely-charged molecules of the proteins in question and charged molecules in the agar gel, (2) the electroendoosmotic flow which is generated in such a gel, and (3) the field strength applied. While the term "electrophoresis" is used almost exclusively in the prior art, it is clear that the principals of electrochromatography were recognized some time ago; see, for example, R. J. Wieme, "Agar Gel Electrophoresis", Elsevier Publishing Company, Amsterdam, 1965, pages 192-195. Accordingly, the term "electrochromatography" is used throughout this disclosure to refer to electrophotoresis-type separations of proteins on agar gel under acidic conditions.

The method of the present invention requires the use of an agar gel having a wet thickness of from about 0.1 to about 0.5 mm. The nature of the agar is not critical, although the pH of the citrate gel buffer to some extent is dependent upon the nature and character of the agar employed. That is, agar having fewer negative charges contained therein typically requires a slightly different buffer pH. However, the pH required still will lie within the range discussed hereinbelow, and the optimu pH is readily determined by those having ordinary skill in the art. Suitable agar preparations are readily available commercially and have been found to be suitable in the method of the present invention. The amount of agar employed typically is about 2% weight per volume. It will be apparent to those having ordinary skill in the art, however, that greater or lesser amounts of agar, such as from about 1 to about 3%, can be employed, provided that appropriate adjustments in the other parameters are made. As a general rule, however, agar concentrations of less than about 1% weight per volume, typically are not suitable.

Optionally, the gel can contain minor amounts, e.g. less than about 10% weight per volume, of one or more humectants. Examples of suitable humectants include sucrose, hydroxethylcellulose, glycerol, sorbitol, and the like. A particularly useful amount of humectant is from about 4 to about 6%, with sucrose and sorbitol being the preferred materials. The humectant aids in the retention of small amounts of water at the surface, thereby stabilizing the wet film. The humectant also serves as a dried film stabilizing agent. The use of a humectant is preferred, with a combination of 4% sorbitol and 1% glycerol being especially suitable.

In addition, the gel also can contain a small amount of a wetting agent which acts as a dried film stabilizing agent. The use of a wetting agent is, in practice, preferred. Typically, the wetting agent will be present in an amount less than about 0.1% weight per volume. The suitable wetting agents include anionic and nonionic surfactants, as well as other compounds having properties of a wetting agent. Examples of such compounds include, among others, polyvinyl alcohol, sulfate esters of alkyl phenoxy polyoxyalkylene alkanols, alkyl aryl sulfonates, alkali metal salts of the sulfates and sulfonates, fatty acid soaps, polyether alcohols, and the like. In addition to polyvinyl alcohol, specific examples of such wetting agents include, among others, nonyl phenyl polyoxyethylene sulfate, sodium lauryl sulfate, and nonyl phenyl polyoxyethylene ethanol. It may be noted that when polyvinyl alcohol is employed, such material should be essentially free of polyvinyl acetate.

The citrate gel buffer can have a citrate concentration of from about 0.02 to about 0.05 M and is prepared by known procedures. Typically, the desired amount of sodium citrate dihydrate is dissolved in an appropriate amount of water, to which solution is added an aqueous solution of citric acid until the desired pH is reached. A particularly useful citrate concentration is 0.0375 M. In general, the citrate gel buffer can have a pH of from about 5.8 to about 6.8, with a pH of from about 6.0 to about 6.3 being preferred. As already indicated, it often is necessary to make minor adjustments in the gel buffer pH, depending upon the nature and character of the agar employed in preparing the gel.

The citrate well buffer is prepared essentially as described for the gel buffer. The well buffer in general will have a citrate concentration of from about 0.05 to about 0.1 M and a pH of from about 6.0 to about 6.5. A particularly useful citrate concentration is about 0.1 M, and the preferred pH is from about 6.0 to about 6.3.

As already pointed out, the gel must have a thickness of from about 0.1 to about 0.5 mm. A particularly preferred wet thickness is from about 0.3 to about 0.4 mm. While the gel can be prepared by any known method, a most convenient means of gel preparation is the use of cassette-type molds, such as are disclosed in U.S. Pat. Nos. 3,499,265 and 3,635,808.

In general, the electrochromatography is carried out in accordance with well known procedures which are common for electrophoresis. In general, the field strength can vary from about 5 to about 20 volts per cm. The preferred field strength is 10 volts per cm. Under the conditions of the preferred field strength, the electrochromatography procedure typically will take from about 30 to about 45 minutes. The precise time required however is not critical and is essentially a function of the other parameters involved.

Materials and Methods. If desired, the amount of glycosylated hemoglobins thus separated can be estimated by visually inspecting the gel. Such amount can be quantitated, however, by various known methods. For example, the gel can be scanned directly in a densitometer, taking advantage of the heme's maximum absorbance at 420 nm. In practice, such direct scanning procedure is preferred since it permits the use of a simplified procedure for preparing hemolysates.

Such simplified procedure consists of mixing one part of whole blood with two parts of water containing 0.1% weight per volume of saponin. A volume of the resulting mixture, typically 0.8 $\mu$l, then is applied to the gel sample well.

Alternatively, the amount of glycosylated hemoglobin can be quantitated indirectly by staining the fractions with a nonspecific protein stain such as amido black or Ponceau S, followed by scanning the gel in a densitometer at an appropriate wavelength. When such a staining procedure is employed, however, the sample hemolysates must be prepared from processed erythrocytes, since non-heme protein can not be present when a general protein stain is used. The preparation of hemolysates from processed erythrocytes is, of course, well known to those skilled in the art since such preparations are commonly used in all chromatographic assays for glycosylated hemoglobins.

Other methods for quantitating the amount of glycosylated hemoglobin will be readily apparent to those having ordinary skill in the art.

Gel Buffer. The gel buffere, having a citrate concentration of 0.0375 M and a pH of 6.0 at room temperature, was prepared by dissolving 11.03 g. of sodium citrate dihydrate in one liter of deionized distilled water. The pH of the resulting solution was adjusted to 6.0 by adding a sufficient amount of a 0.0375 M citric acid solution prepared by dissolving 7.20 g. of citric acid in one liter of deionized distilled water.

Agar. The gel solution was prepared by combining 2.0 g. of Baco-agar (Difco), 4.0 g. of sorbitol, 1.0 ml. of glycerol, and 2.0 mg. of sodium azide with 100 ml. of gel buffer. The resulting mixture was heated, with stirring, in a boiling water bath for 30 minutes after total dissolution of the components had occurred.

Preparation of Gel Films. Empty cassette molds were obtained from Corning Medical (Corning Glass Works, Medfield, Massachusetts) and used to form the thin gels. The gel solution was cooled to 65-70° before being injected into the lower nipple of the mold with a glass syringe to which a piece of plastic tubing, 3 mm. in diameter, was attached. The mold was held in an upright position during injection to facilitate removal of air from the upper nipple. After injecting about 5 ml. of gel, the cassette mold was placed on a flat benchtop, and a flat weight of about 500 g. was placed on the mold to expel any excess gel solution. After the gel had set (about 5 minutes at ambient temperature), each gel was wrapped in a stretch plastic and aluminum foil and stored at 4° for 24 hours before use. The gels thus prepared were stable for at least 6 months if kept tightly sealed and a preservative were present.

Well Buffer. Well buffer, having a citrate concentration of 0.1 M and a pH of 6.0 at room temperature, was prepared by dissolving 29.41 g. of sodium citrate dihydrate in one liter of deonized distilled water. The pH of the resulting solution was adjusted to 6.0 by adding a sufficient amount of a 0.1 M citric acid solution prepared by dissolving 19.21 g. of citric acid in one liter of deionized distilled water.

Electrochromatography. Hemoglobin $A_0$ and $A_{1c}$ standards were obtained by preparative column chromatography in accordance with the procedure of Trivelli, supra. Human blood samples were obtained from a local hospital (Corning Hospital, Corning, New York). The apparatus employed was the Corning Medical electrophoresis cell connected by leads to a Corning Medical power supply adapted to a constant 60 volt output. Hemolysates were prepared according to the Corning Medical Electrophoresis Operations Procedures Manual or by thoroughly mixing whole blood (1 part) with 0.1% weight per volume aqueous saponin solution (2 parts). Typically, 0.8 μl. of hemolysate (approximately 40 μg. of total hemoglobin) was applied to each sample well.

Each well of the electrophoresis cell base was filled with 90 ml. of well buffer. Gels were placed in the gel holder-cover and set into the cell base so that the gel edges were immersed in buffer. A constant field strength of 10 volts per cm. was applied for approximately 30 minutes.

Visualization and Quantitation. At the completion of the electrochromatographic separation procedure, gels were visualized and quantitated in either of two ways. In the preferred way, the gel was removed from the electrophoresis cell and dried in a Corning Medical drying oven at about 63° for about 15 minutes. The dried gel then was directly scanned in a Corning Medical Model 720 densitometer fitted with a 420 nm filter.

Alternatively, the gel was stained with either amido black or Ponceau S. Each stain was prepared by dissolving 1.0–2.0 g. of the dye in one liter of 5% by volume aqueous acetic acid. Stain times were 5–10 minutes, after which each gel was rinsed in 5% aqueous acetic acid and then dried in a Corning Medical drying oven for 20 minutes. The dried gel was completely destained in the dilute acetic acid solution and rinsed in fresh destaining solution to completely remove background color. The glycosylated hemoglobins were quantitated by scanning the gels in a Corning Medical densitometer at 600 nm for amido black and 520 nm for Ponceau S.

The precision of the direct quantitation procedure was determined by repeatedly running a normal human hemolysate and two diabetic human hemolysates, followed by the direct scanning of the gels at 420 nm. The data obtained are summarized in Table I.

TABLE I

Precision of HbA, Analyses on Whole Blood Hemolysate Using Direct Scanning at 420 nm

| Normal Blood | Diabetic Blood A | Diabetic Blood B |
| --- | --- | --- |
| 6.5 | 10.0 | 19.2 |
| 6.4 | 10.0 | 19.1 |
| 6.8 | 10.4 | 19.1 |
| 6.0 | 10.2 | 19.2 |
| 6.5 | 10.2 | 20.0 |
| 6.7 | 10.2 | 18.9 |
| 6.7 | 10.0 | 19.4 |
| 6.2 | 9.8 | 18.7 |
| 6.4 | 10.4 | 18.6 |
| 6.9 | 10.6 | 19.6 |
| 6.6 | 9.4 | 19.6 |
| 6.7 | 9.7 | 19.2 |

With the normal blood hemolysate, the mean was 6.53. The standard deviation was 0.26 and the coefficient of variation was 4%. The blood glucose value was 85 mg-%.

With the diabetic blood hemolysates, the means were 10.08 and 19.22, respectively, and the standards of deviation were 0.33 and 0.4, respectively. The coefficients of variation were 3.3% and 2.1%, respectively. The blood glucose values were 158 mg-% and 348 mg-%, respectively.

The separation accuracy and precision of the indirect quantitation procedure also were determined. To determine separation accuracy, premixed, standard samples of hemoglobin $A_{1c}$ and hemoglobin $A_0$ having known or predetermined amounts of hemoglobin $A_{1c}$ present were subjected to the method of the present invention. The samples involved hemoglobin $A_{1c}$ contents of from 5% to 50%. Using four determinations per sample, the average of such four determinations at each level of hemoglobin $A_{1c}$ are summarized in Table II.

TABLE II

Separation Accuracy, Premixed Standard Samples of $HbA_{1c}$ and $HbAo$ (Individually Determined by Drabkin Procedure in Given Ratios)

| Expected Value Found (4 determ.) | 5% | 10% | 50% |
| --- | --- | --- | --- |
| Amido Black Stain | 5.45 | 10.1 | 53.1 |
| Ponceau S Stain | 5.83 | 11.1 | 49.7 |

The precision of the assay was determined by repeatedly running normal human hemolysate and visualizing with either amido black or Ponceau S stain. The data obtained are summarized in Table III.

TABLE III

Precision of the Assay Normal Human Hemolysate Assayed Repeatedly

| Amido Black Stain (600nm) | | | Ponceau S Stain (520nm) | |
| --- | --- | --- | --- | --- |
| S#1:6.3 | #6:5.9 | #11:6.3 | S#1:8.1 | #5:7.2 |
| 2:6.6 | 7:6.2 | 12:6.6 | 2:7.6 | 6:7.1 |
| 3:6.7 | 8:6.7 | 13:6.9 | 3:7.4 | 7:7.7 |
| 4:7.2 | 9:5.9 | | 4:7.5 | 8:7.0 |
| 5:6.2 | 10:6.14 | | | |

The data in Table III were subjected to statistical analyses. With amido black stain and 13 samples, the mean value was 6.43, with a standard deviation of 0.39. The standard error of the mean was 0.11. Similarly, using 8 samples and Ponceau S stain, the mean value was 7.45. The standard deviation was 0.36, and the standard error of the mean was 0.13.

What is claimed is:

1. In a method for discretely separating glycohemoglobins from nonglycosylated hemoglobins by citrate agar gel electrochromatography in which the gel buffer has a citrate concentration of 0.05 M and a pH of 6.2, the improvement which comprises employing:
   A. an agar gel having a wet thickness of from about 0.1 to about 0.5 mm.,
   B. a citrate gel buffer having a citrate concentration of from about 0.02 to about 0.05 M and a pH of from about 5.8 to about 6.8,
   C. a citrate well buffer having a citrate concentration of from about 0.05 to about 0.1 M and a pH of from about 6.0 to about 6.5, and
   D. a field strength of from about 5 to about 20 volts per cm.

2. The method of claim 1 in which the gel wet thickness is from about 0.3 to about 0.4 mm.

3. The method of claim 1 in which the gel buffer has a citrate concentration of about 0.038 M.

4. The method of claim 1 in which the gel buffer has a pH of from about 6.0 to about 6.3.

5. The method of claim 1 in which the well buffer has a citrate concentration of about 0.1 M.

6. The method of claim 1 in which the well buffer has a pH of from about 6.0 to about 6.3.

7. The method of claim 6 in which the well buffer has a pH of about 6.0.

8. The method of claim 1 in which the field strength is about 10 volts per cm.

9. The method of claim 1 in which the gel contains a humectant at a level of from 0 to about 10% weight per volume.

10. The method of claim 9 in which the humectant is sorbitol.

11. The method of claim 1 in which the sorbitol is present at a level of about 4% weight per volume.

12. The method of claim 1 in which the humectant is glycerol.

13. The method of claim 1 in which the glycerol is present at a level of about 1.3% weight per volume.

14. The method of claim 1 in which the humectant is a mixture of sorbitol and glycerol.

15. The method of claim 14 in which the sorbitol and glycerol are present at levels of about 4% weight per volume and about 1.3% weight per volume, respectively.

16. The method of claim 1 in which the gel contains a wetting agent at a level of from 0 to about 0.1% weight per volume.

17. The method of claim 16 in which the wetting agent is polyvinyl alcohol.

18. The method of claim 17 in which the polyvinyl alcohol is present at a level of about 0.017% weight per volume.

* * * * *